Figure 3:
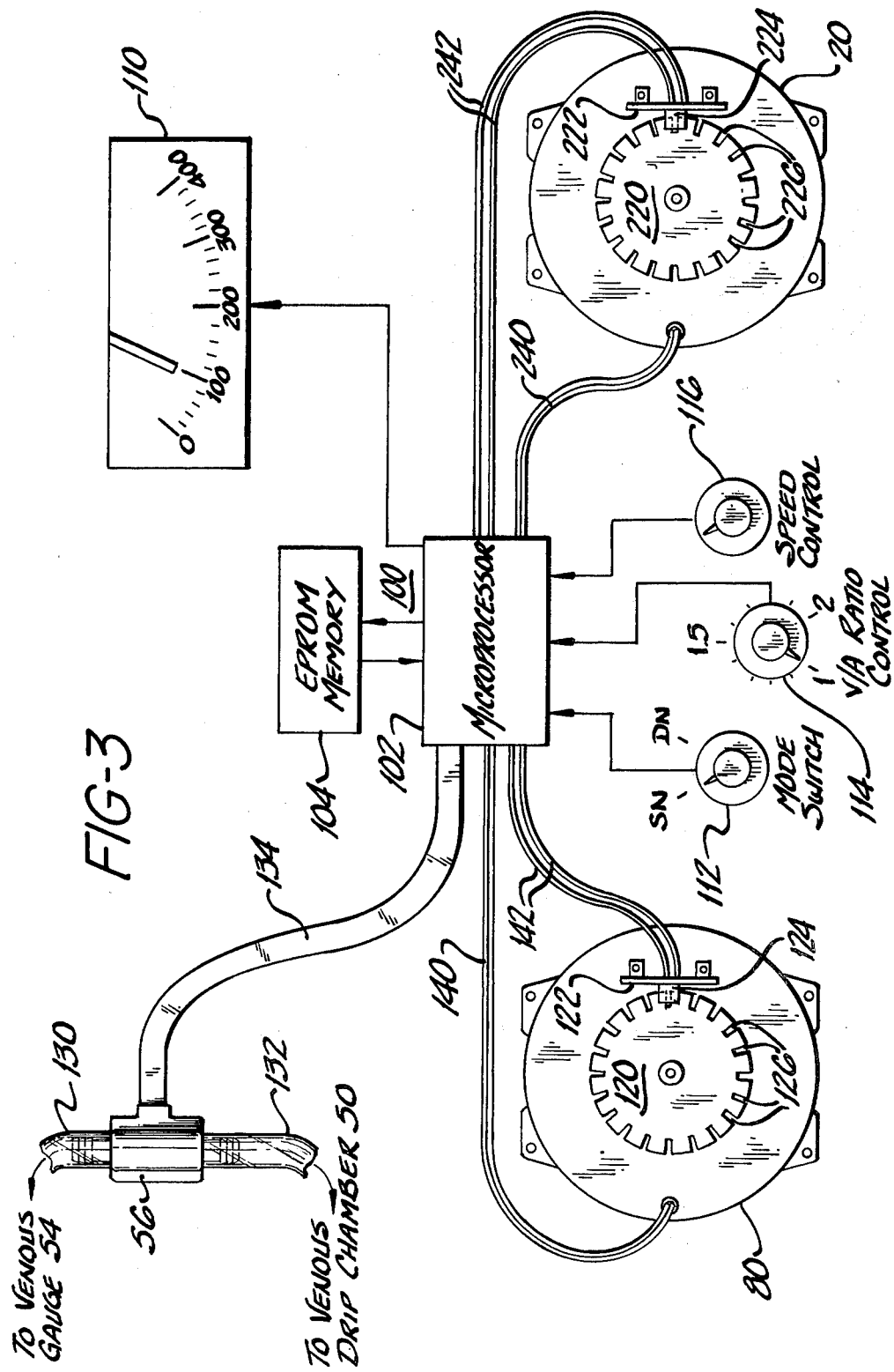

United States Patent [19]

Troutner et al.

[11] Patent Number: 4,464,164
[45] Date of Patent: Aug. 7, 1984

[54] FLOWRATE CONTROL FOR A BLOOD FLOW SYSTEM

[75] Inventors: Vernon H. Troutner, St. Petersburg; Richard A. Morrow, Tarpon Springs, both of Fla.

[73] Assignee: Extracorporeal Medical Specialties, Inc., King of Prussia, Pa.

[21] Appl. No.: 423,381

[22] Filed: Sep. 24, 1982

[51] Int. Cl.³ .............................................. A61M 1/03
[52] U.S. Cl. ................................... 604/5; 128/DIG. 3
[58] Field of Search ................. 604/4, 5; 128/DIG. 3; 210/321.2, 321.3

[56] References Cited

U.S. PATENT DOCUMENTS

| | | | |
|---|---|---|---|
| 3,756,234 | 9/1973 | Kopp | 128/214 R |
| 3,830,234 | 8/1974 | Kopp | 128/214 R |
| 3,848,592 | 11/1974 | Willock | 128/214 R |
| 3,902,490 | 9/1975 | Jacobsen et al. | 604/5 X |
| 3,985,134 | 10/1976 | Lissot et al. | 128/214 R |
| 4,231,366 | 11/1980 | Schael | 128/214 E |
| 4,401,431 | 8/1983 | Arp | 604/4 |

FOREIGN PATENT DOCUMENTS 2703188  8/1978  Fed. Rep. of Germany .......... 604/5

OTHER PUBLICATIONS

"New System for Single-Needle Dialysis", British Medical Journal, vol. 281, p. 1109, (Oct. 25, 1980).

Primary Examiner—Edward M. Coven
Attorney, Agent, or Firm—Mark A. Hofer; W. Brinton Yorks, Jr.

[57] ABSTRACT

Blood flowrate in a hemodialysis system is controlled in accordance with the relative speeds of two periodically operated blood pumps. Information as to the speeds of the two pumps is converted to flowrate information, which is used to determine the mean flowrate of blood through the system. The mean blood flowrate may be altered by changing the speeds of the blood pumps in a control system which maintains a constant ratio of pump speeds.

7 Claims, 5 Drawing Figures

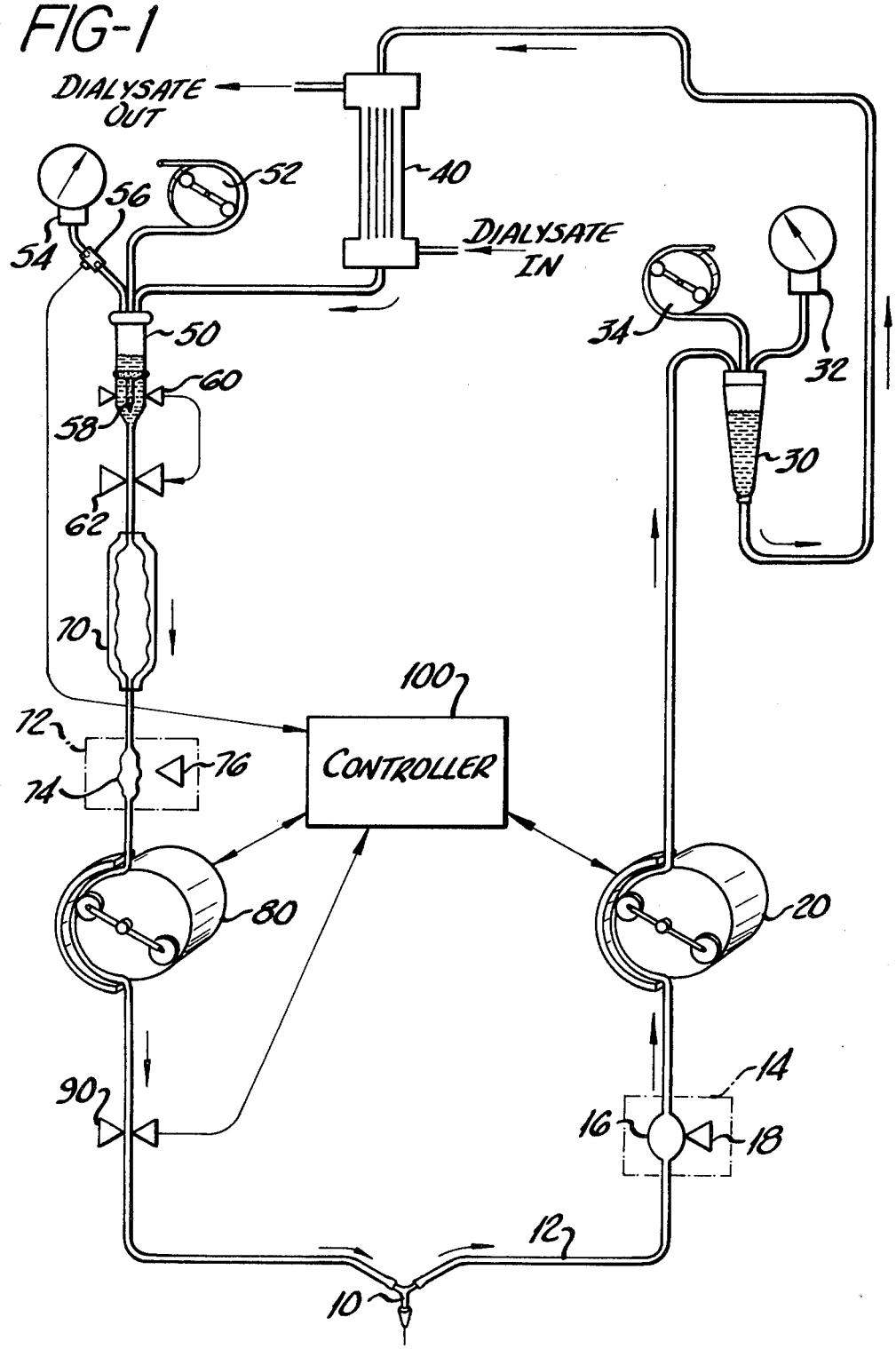

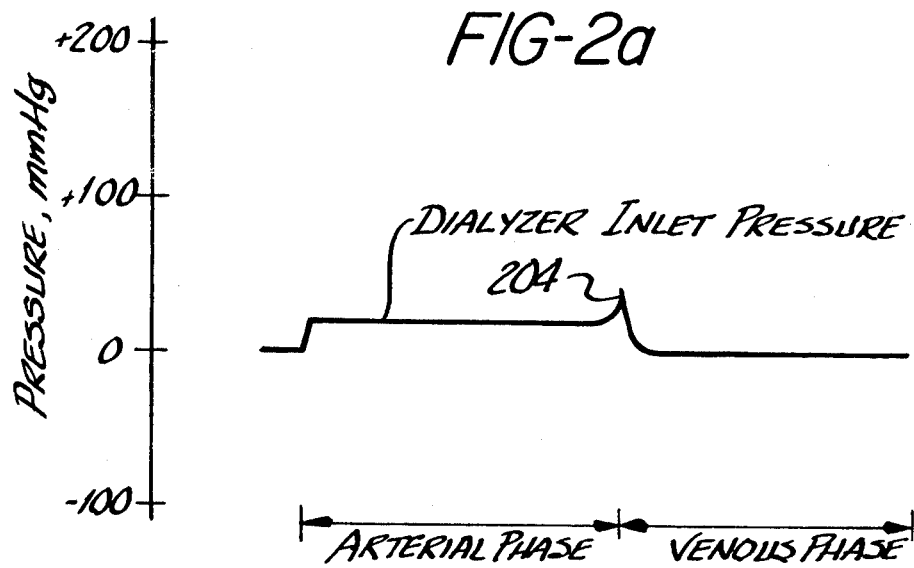
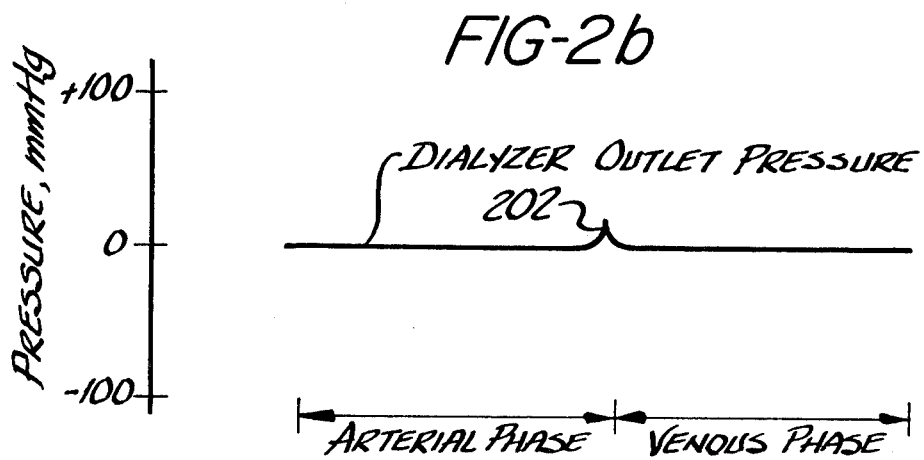

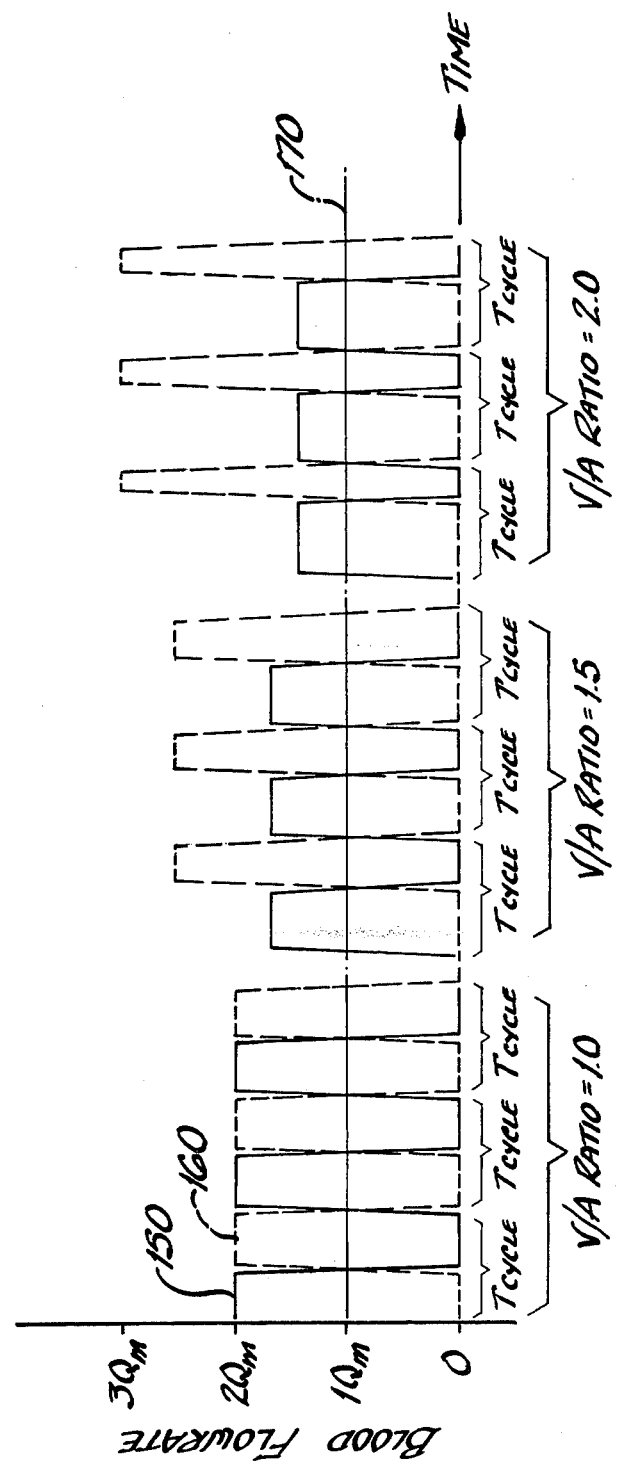

FLOWRATE CONTROL FOR A BLOOD FLOW SYSTEM

This invention relates to flowrate control for a blood flow system and, in particular, to blood flowrate control in a closed loop blood flow arrangement using either one or two blood pumps.

Hemodialysis blood flow systems are employed as a therapeutic measure when a patient's kidneys no longer perform their blood purifying function by reason of disease, removal or other malfunction. Kidney failure results in the accumulation of toxic wastes in the patient's blood. Unless measures are taken to remove these wastes, the patient will experience potentially fatal uremic poisoning. Uremic poisoning may be prevented through the use of hemodialysis, by which blood is drawn from the patient and circulated through a dialyzer. In the dialyzer, the blood is separated from a specially treated dialysate fluid by a membrane which has pores of microscopic size through which waste products from the blood may pass. The microscopic pores are too small, however, to permit the passage of blood cells, proteins, and other essential elements of the blood through the membrane. The waste products thus diffuse into the dialysate fluid and are removed from the patient's blood. The purified blood is then returned to the patient's body.

In many conventional hemodialysis systems, such as the Single Patient System (SPS) Model DM-350 produced by Extracorporeal Inc. of King of Prussia, Pa., blood is extracted from the patient through a first arterial venipuncture, which may typically be formed in a cannulation procedure. The blood is then processed by the SPS system and returned to the patient's body through a second, venous venipuncture, which may also comprise a cannula. A single, arterial blood pump is used in the SPS system to circulate the patient's blood through the system.

In other known hemodialysis systems, blood is extracted from and returned to the patient's circulatory system through a single needle with a Y-shaped junction. In such a hemodialysis system, blood may be alternately cycled from and to the patient's body by a single blood pump, or by arterial and venous blood pumps, respectively. During the first, or arterial, phase of operation, blood is drawn from the patient and pumped into the dialysis system by the arterial blood pump. Blood is prevented from returning to the needle by the closure of a valve located between the outlet of the arterial pump and the needle, or through a clamping action of the venous blood pump. Blood pressure within the system builds until a time at which the arterial pump is turned off, the valve is opened, or the venous pump in a two-pump system is turned on to pump the blood out of the dialysis system and back to the patient during a second, venous phase of operation. After the return of a desired amount of blood to the patient, the venous phase is terminated and the cycle repeats.

Each type of hemodialysis system has advantages which can vary from patient to patient. For instance, the single needle system offers the advantage of half the number of needle insertions, which may be psychologically attractive to the patient, as well as possibly prolonging the life of the fistula into which the needle in normally inserted. However, if a patient has low blood flow rates, hemodialysis through a single needle may not be practical, and the use of a double needle system may be necessitated. In addition, single needle systems frequently require larger needles which are difficult to insert, and blood recirculation through the hemodialysis system may be high if blood flow through the fistula is low. It is therefore desirable for a hemodialysis system to be capable of operation in either a single needle mode or a double needle mode so as to be of use to a wider variety of patients.

In both the double needle, single blood pump system and the single needle, two blood pump system, it is necessary to be able to accurately control the blood pumps to maintain a desired blood flowrate. Not only must the blood flowrate be constantly monitored and controlled, but flowrate information must also be displayed in a useable manner, and should also be used to activate warning devices when blood flow parameters deviate from their desired ranges of values. It is thus desirable to detect and process blood flowrate information in both single and double blood pump systems, and to use the information to properly control the operation of the system.

In accordance with the principles of the present invention, a closed loop blood flow system is provided, including a first, arterial blood pump for withdrawing blood from a patient and a second, venous blood pump for returning the blood to the patient. A first control is connected to both pumps to allow the speed of the pumps to be established. A second control is operatively connected to the first control, the two pumps, and to control signal processing apparatus to permit setting of the speed ratio of the two pumps. The control signal processing apparatus is responsive to both the speed and ratio settings to develop speed control signals for the two pumps which maintain the desired speed ratio.

In accordance with a further aspect of the present invention, the control signal processing apparatus monitors the pump speeds and is responsive to pump speed information for developing a signal which indicates the mean blood flowrate. In a preferred embodiment of the present invention, the control signal processing apparatus monitors rotational information of each pump. The rotational information is then converted to information indicative of the blood flowrate of each pump. The control signal processing apparatus then determines the mean blood flowrate, $Q_M$, for display on a display device. The mean blood flowrate $Q_M$ is determined in accordance with the expression $$Q_M = \frac{R}{R+1} Q_A,$$

where R is the pump ratio, equal to the venous pump flowrate divided by the arterial pump flowrate and $Q_A$ is the arterial blood pump flowrate. By observing the mean blood flowrate, the first (speed) control may be adjusted to alter the mean blood flowrate and hence the rate of dialysis.

In accordance with still another aspect of the present invention, the blood flow system is capable of operation using only the arterial blood pump for blood circulation. In this mode of operation, the first control sets the speed of the arterial blood pump, and the control signal processing apparatus displays the flowrate equivalent of the speed of the arterial blood pump on the display device. In this single pump mode, the second, ratio control has no effect on system operation. In the drawings:

FIG. 1 illustrates the blood circulation path of a hemodialysis system constructed in accordance with the principles of the present invention;

FIGS. 2a and 2b graphically represent blood pressure at the inlet and the outlet of the dialyzer of FIG. 1;

FIG. 3 illustrates in greater detail the control system for the venous and arterial blood pumps of the arrangement of FIG. 1; and FIG. 4 graphically represents the mean blood flowrate of the arrangement of FIG. 1 for different pump flowrate ratios.

Referring to FIG. 1, the blood flow path of a single needle hemodialysis system is shown, including a single needle 10 suitable for the transfer of blood from and to a patient. In FIG. 1, the arrows indicate the direction of the flow of blood through the system.

From the single needle 10, blood flows through the blood tubing 12 to a negative pressure pillow switch 14. The pillow switch 14 includes a pillow-like section of tubing 16 and a sensor or switch 18 which is responsive to a relaxation of pressure in the pillow-like section 16. When the pillow pressure declines below a certain level the sensor or switch responds by initiating a system alarm as well as other procedures which interrupt the operation of the system.

From the pillow switch 14 the blood tubing is connected through an arterial roller blood pump 20. The arterial blood pump 20 operates under control of a controller 100, as will be described subsequently. The blood tubing is then connected to a post-pump arterial drip chamber 30 which collects blood and accommodates the connection of various gauges to the system. The pressure in the drip chamber 30 is monitored by an arterial mechanical gauge 32 with alarm contacts. The blood level within the chamber 30 may be varied through the operation of a blood level adjust roller pump 34, by which air may be added to or subtracted from the chamber. The outlet of the drip chamber 30 is connected by blood tubing to the inlet of a capillary dialyzer 40. In the dialyzer, impurities in the blood pass through the dialyzer membrane and into dialysate fluid, which flows into and out of the dialyzer through separate ports under control of a dialysate preparation system (not shown).

Purified blood flows out of the dialyzer 40 and into a venous drip chamber 50. The pressure within the venous drip chamber 50 is monitored by a mechanical venous pressure gauge 54 with alarm contacts. A second blood level adjust pump 52 is connected to the drip chamber 50 to add or subtract air from the chamber, thereby adjusting the blood level within the chamber. In a tubing line between the venous drip chamber 50 and the venous pressure gauge 54 is a solid state pressure transducer 56 which controls the cycling of the blood pumps and also provides another monitor of venous blood pressure. The venous drip chamber 50 further includes a filter 58 located within the chamber.

An air/foam detector 60 is located next to the venous drip chamber 50. The detector 60 ultrasonically or optically detects the presence of an abnormal amount of air or foam in the blood and also monitors the blood level in the chamber 50. The detector responds to the occurence of such an abnormality by activating a clamp 62, which clamps the blood tubing closed to prevent the pumping of foam and air bubbles into the patient's circulatory system.

The blood tubing is then connected to the inlet of a vinyl accumulator bag 70. The outlet of the accumulator bag 70 is coupled to a positive pressure pillow switch 72, which may be merely an extension of the accumulator bag 70 or, as shown in FIG. 1, may include its own pillow-shaped tubing section 74. Abnormal expansion of the pillow-shaped section 74 in response to an undesirable buildup of blood pressure causes the sensor or switch portion 76 to set off an alarm and to interrupt system operation.

From the pillow switch 72 the blood tubing passes through a venous roller blood pump 80 which is operated under control of the controller 100. The blood tubing then passes through a second air/foam detector 90, which is connected into the system alarm by the controller 100. Finally, the blood tubing is connected to the needle 10 to return the purified blood to the patient's circulatory system. The arrangement of FIG. 1 is described more fully in concurrently filed U.S. patent application Ser. No. 423,380, entitled "SINGLE NEEDLE ALTERNATING BLOOD FLOW SYSTEM".

In operation, the arterial blood pump 20 of FIG. 1 is activated by the controller 100 to begin withdrawing blood from the patient through the needle 10. The negative pressure pillow switch safeguards against the withdrawal of blood at too great a rate, as indicated by the development of a negative pressure at the switch. Withdrawal of blood at too great a rate by the arterial pump can lead to occlusion of the patient's fistula, blood foaming or recirculation of purified blood at the needle junction. The pillow switch also guards against any blockage of blood flow in the fistula and needle.

The patient's blood is pumped through the blood tubing 12, the arterial drip chamber 30, and into the dialyzer 40. The flow of blood is virtually unimpeded up to the dialyzer, at which point the pressure developed by the arterial pump forces the blood through the capillaries of the dialyzer. The dialyzer constitutes the only significant pressure drop between the arterial blood pump 20 and the accumulator bag. This pressure drop will vary with the type of dialyzer. FIG. 2a illustrates the typical inlet pressure of a capillary-type dialyzer. During the arterial phase of operation, when the arterial blood pump 20 is running, the dialyzer inlet pressure in this example is seen to remain substantially at 20 to 25 mm Hg relative to atmospheric pressure, which would be indicated on the arterial gauge 32.

At the outlet of the dialyzer, however, blood pressure remains substantially at 0 mm Hg (gauge), as shown in FIG. 2b. This is because the purified blood is free to flow into the venous drip chamber 50, and then into the accumulator bag 70. The accumulator bag is initially empty, and easily fills with blood from the drip chamber, since the outside of the bag is referenced to atmospheric pressure. Thus, as the accumulator bag fills, it produces substantially no back pressure which would impede the flow of blood out of the dialyzer. Furthermore, since the accumulator bag is referenced to atmospheric pressure, the pressure sensing devices at the outlet side of the dialyzer, such as the venous pressure gauge 54 and the pressure transducer 56, can indicate the accumulator bag pressure directly by being similarly referenced to atmospheric pressure.

The accumulator bag fills freely with blood until full, which may typically be a capacity of 70 ml., at which time its expansive limits are approached and the pressure in the accumulator bag and venous drip chamber begins to rise, as indicated at 202 in FIG. 2b. This rise in pressure is translated back to the inlet side of the dialyzer, as shown at 204 in FIG. 2a. The rise in pressure is indicated by both the arterial and venous mechanical gauges 32 and 54, and is also sensed by the solid state pressure transducer 56. The electrical signal produced by the transducer 56 begins to change, and the changing value is applied to the controller 100. The controller responds to the attainment of a voltage indicative of a predetermined pressure in the venous drip chamber by stopping operation of the arterial blood pump 20 and initiating operation of the venous blood pump 80. In the example of FIG. 2b, the dialyzer outlet pressure at which the arterial pump is turned off is seen to be approximately 20 mm Hg. The positive pressure pillow switch 72 guards against the attainment of an unusually high venous pressure by shutting down the system if such pressures are approached.

The venous blood pump 80 is operated for a given number of cycles to remove the blood from the accumulator bag and return it to the patient's system. Pump cycles may be used as the measure of this venous phase of operation since each pump cycle corresponds to the pumping of a known volume of blood. The number of pump cycles required to empty the accumulator bag may also be determined since the capacity of the bag when full is a known quantity, the blood levels in the drip chambers 30 and 50 may be controlled by the blood level adjust pumps 34 and 52, and the blood tubing system is essentially noncompliant and has a predictable blood capacity.

As blood is returned to the patient the venous pressure at the outlet of the dialyzer rapidly falls back to zero mm gauge, as shown in FIG. 2b, as the accumulator bag quickly relaxes. At the same time, the blood pressure at the inlet side of the dialyzer drops back toward zero gauge pressure since the arterial blood pump is turned off. This means that blood flow through the dialyzer occurs primarily during the arterial phase of the system, when the arterial blood pump is forcing blood through the dialyzer. Since the dialyzer pressure does not go below zero as the accumulator bag is emptied, undesirable negative transmembrane pressures are not produced in the system. While the blood is being returned to the patient during the venous phase, the air/foam detector 90 monitors the returning blood and alerts the controller 100 if an undesirable amount of air or foam is contained in the blood. When the desired amount of blood has been returned to the patient, the controller terminates the venous phase by stopping the blood pump 80 and initiates operation of the arterial pump 20 to begin another arterial phase of operation. This phasing of pump operation is described in detail in concurrently filed U.S. patent application Ser. No. 423,378, entitled "DUAL PHASE BLOOD FLOW SYSTEM AND METHOD OF OPERATION".

The control arrangement for the venous and arterial pumps of FIG. 1 is shown in greater detail in FIG. 3. The solid state pressure transducer 56 has one port connected by way of a tubing segment 130 to the venous pressure gauge 54 (not shown in FIG. 3), and a second port connected by way of a tubing segment 132 to the venous drip chamber 50 (not shown in FIG. 3). The pressure transducer 56 is illustrated as a flow-through type comprising an open-ended tube located between the two ports. A silicon chip sensing element is bonded to the side of the tube, and contains a sensing diaphragm and piezoresistors. As the pressure within the tube changes, the diaphragm flexes, changing the resistance of the piezoresistors and resulting in an output voltage proportional to pressure. This output voltage is communicated to an input of microprocessor 102 of controller 100 by way of a cable 134.

Outputs of the microprocessor 102 are coupled to the motor of arterial pump 20 by a power cable 240 and to the motor of venous pump 80 by a power cable 140. The microprocessor 102 is also connected to the arterial and venous pumps by wires 242 and 142, respectively. The wires 242 and 142 convey motor speed information to the microprocessor from slot encoders connected to the shafts of the pump motors. Each slot encoder includes a slotted disc 120, 220 mounted on the shaft of the pump motor, an optical detector 124, 224 and a circuit board 122, 222. As each slotted disc 120, 220 turns on the motor shaft, the slots 126, 226 along the perimeter of the disc are sensed by optical detectors 124, 224, respectively, and are indicated by pulses produced by circuitry on respective circuit boards 122, 222. The pulses are applied to the microprocessor 102 by way of wires 142, 242, thereby providing the microprocessor with an indication of the motor speeds of the arterial and venous pumps.

As described above, the venous pump 80 is operated for a predetermined number of pump turns, which is monitored by the controller 100 by receipt of information from the venous pump slot encoder. Since each pump turn corresponds to the transmission of a known volume of blood, operating the venous pump for a predetermined number of turns will return a predetermined amount of blood through the needle 10. In a working embodiment of the present invention, the pump motor turns the roller of the pump through a reduction system such that the motor shaft, and hence the slotted disc 120, rotates 49 times for each turn of the pump roller. When the disc contains 20 slots around its perimeter, 980 pulses will be produced by the slot encoder during one pump roller turn. Thus, fractions of roller turns, and hence small units of blood flow, may be measured precisely. Once the venous pump has completed a predetermined number of pump turns, the venous pump is stopped and the arterial pump is turned on to begin another arterial phase.

The microprocessor 102 also receives input signal information from a mode switch 112, a venous/arterial ratio control 114, and a speed control 116. The information received by the microprocessor 102 is used as data for a control program stored in an EPROM memory 104, which is connected to the microprocessor 102. The microprocessor also controls the reading of a flowrate meter 110, which is calibrated to read in units of milliliters of blood per minute.

The microprocessor 102 of FIG. 3 will control the elements of the hemodialysis system of FIG. 1 in accordance with a single needle control program or a double needle control program stored in the memory 104. Mode of operation, and hence program selection, is accomplished by setting mode switch 112 for the desired mode. When the single needle mode (SN) is selected, the system operates using all of the elements shown in FIGS. 1 and 3 to perform hemodialysis. When the double needle mode (DN) is selected, the system of FIGS. 1 and 3 will perform double needle hemodialysis using only the arterial blood pump 20 as the sole blood pump in the system. These modes of operation are more fully described in concurrently filed U.S. patent application Ser. No. 423,376, entitled "DUAL MODE HEMODIALYSIS SYSTEM".

During both modes of operation, it is desirable to monitor and control blood flowrate through the system.

In the double needle mode, when the arterial blood pump is the sole blood pump in the system, the microprocessor receives pulses from the slot encoder of the arterial pump 20. The pulse rate is indicative of the speed of the arterial blood pump, and is translated by the microprocessor 102 into a voltage value representative of blood flowrate through the pump. This voltage is applied to flowrate meter 110 to indicate blood flowrate through the hemodialysis system. If the indicated blood flowrate is higher or lower than desired, the speed control 116 is adjusted accordingly to alter the speed of the arterial blood pump, and hence the blood flowrate. Absent the development of a fault condition, the arterial blood pump runs continuously during the double needle mode.

In the single needle mode, however, it is not the flowrate of the individual pumps which is of primary importance, but rather the net rate of blood flow through the system, denoted as the mean blood flowrate. The mean blood flowrate is a function of both the absolute values of the pump speeds, controlled by the speed control 116, and of the relationship of the pump speeds to each other, which is controlled by the ratio control 114. When the speeds of the two pumps are simultaneously increased by adjustment of the speed control 116, the mean blood flowrate, as indicated on the flowrate meter 110, will increase. Control of the ratio of the speeds of the individual blood pumps advantageously allows the system to operate in a manner which will reduce the possibility of fistula acclusion. In the preferred embodiment of the present invention shown in FIGS. 1 and 3, the ratio control 114 will control the venous-to-arterial pump speeds from a ratio of 1:1 to a ratio of 2:1. At a 1:1 ratio, the speeds of the two pumps are controlled to be the same, and at a 2:1 ratio the speed of the venous pump is twice that of the arterial pump. At the 2:1 ratio, the arterial pump will withdraw blood from the patient's fistula at a relatively low rate, which should tend to reduce the possibility that the fistula will collapse.

The embodiment of the present invention illustrated in FIGS. 1 and 3 has been built and tested, in which the following relationships apply. Each pump motor shaft was fitted with a twenty-slot disc 120, 220, and each pump was driven with reduction gearing such that approximately 49 motor revolutions resulted in one pump roller turn. Thus, 20 slots times 49 yields 980 slot encoder output pulses per pump roller turn. When a pump tubing segment with an internal diameter of 5/16 inches was used in each pump, approximately 16 ml of blood was delivered during each pump turn. The microprocessor was programmed to count slot encoder pulses as a function of real time, thereby permitting a determination of the flowrates of the two pumps, $Q_V$ (venous pump flowrate) and $Q_A$ (arterial pump flowrate).

Once the pump flowrates were determined the pump ratio, R, equal to $Q_V/Q_A$ was determined. Using the pump ratio value, mean flowrate $Q_M$ was determined, using either the expression $$Q_M = \frac{R}{R+1} Q_A, \text{ or } Q_M = \frac{1}{R+1} Q_V.$$

The mean flowrate value $Q_M$ was then translated to an equivalent voltage value to display the mean flowrate on the meter 110. The following table gives examples of the flow relationships for single needle mode operation.

TABLE

| Arterial Pump Output (pulses/min.) | Venous Pump Output (pulses/min.) | Arterial Pump Flowrate $Q_A$ (ml/min.) | Venous Pump Flowrate $Q_V$ (ml/min.) | Pump Ratio $R = Q_V/Q_A$ | Mean Flowrate $Q_M$ (ml/min.) |
|---|---|---|---|---|---|
| — | — | — | — | — | |
| 12,012 | 12,012 | 200 | 200 | 1.0 | 100 |
| 10,010 | 15,015 | 167 | 250 | 1.5 | 100 |
| 9,009 | 18,018 | 150 | 300 | 2.0 | 100 |
| 24,024 | 24,024 | 400 | 400 | 1.0 | 200 |
| 20,020 | 30,030 | 333 | 500 | 1.5 | 200 |
| 18,018 | 36,036 | 300 | 600 | 2.0 | 200 |
| 36,036 | 36,036 | 600 | 600 | 1.0 | 300 |
| 30,030 | 45,045 | 500 | 750 | 1.5 | 300 |
| 27,027 | 54,054 | 450 | 900 | 2.0 | 300 |

The flow relationships illustrated numerically in the Table are represented graphically in FIG. 4, in which the abscissa is divided into cycle time increments $T_{cycle}$ and the ordinate represents blood flowrate in normalized increments of mean flowrate $Q_M$. Each cycle time $T_{cycle}$ is composed of an arterial pumping phase followed by a venous pumping phase. At the leftmost side of the FIGURE the venous to arterial pump speed ratio is set at 1:1. The solid line 150 represents the operation of the arterial blood pump, which is on for the first half of each cycle, and transports blood at a $2Q_M$ flowrate during these times. During the second half of each cycle the venous pump is operational, as indicated by the broken line 160. The venous pump also transports blood at a $2Q_M$ flowrate during the times that it is running. The solid horizontal line 170 represents the mean blood flowrate that is displayed on the flowmeter during this 1:1 ratio of operation, and is seen to be equal to $Q_M$ in accordance with the above equations.

The middle portion of FIG. 4 represents the operating conditions when the speed of the venous pump is set to be 1.5 times that of the arterial pump and the system is to maintain the same mean blood flowrate of $Q_M$. Under these conditions the arterial blood pump is on for approximately the first 60% of the cycle time $T_{cycle}$, and the venous blood pump runs for the remaining 40% of the cycle. The arterial blood pump transports blood at a flowrate of 1.67 $Q_M$ during the time that it is running, and the venous blood pump transports blood at a flowrate of 2.5 $Q_M$, giving the desired ratio R of 1.5. Inserting these values for R and $Q_A$ or $Q_V$ into the above equations yields the desired mean blood flowrate of $Q_M$ illustrated by the horizontal line 170.

The righthand portion of FIG. 4 illustrates system operation for a pump speed ratio setting of 2.0 when the same mean blood flowrate of $Q_M$ is being maintained by the controller. The arterial pump is seen to run during the first two-thirds of each cycle time at a flowrate of approximately 1.5 $Q_M$, and the venous pump runs for the last third of each cycle at a flowrate of approximately 3.0 $Q_M$. These flowrate values, when inserted in the above equation, again are seen to produce the desired mean blood flowrate of $Q_M$ indicated by horizontal line 170.

When system operation in the single needle mode is commenced, it is preferable to first set the ratio control 114 to the desired pump speed ratio. Then, when hemodialysis begins, the mean blood flowrate as indicated on the flowrate meter 110 is noted. If the flowrate is lower or higher than desired, the speed control 116 is then adjusted. The pump speed adjustment is seen to be reflected as a change in the mean blood flowrate, which is the aspect of operation desired to be controlled, as opposed to actual knowledge of the velocities of the pumps.

For example, assume that system operation commences at an indicated mean flowrate of 100 ml/min., and that a mean blood flowrate of 200 ml/min. is desired. The speed control 116 will be adjusted to cause the microprocessor 102 to increase the speeds of the two pumps. The arterial pump will then attain its predetermined pressure threshold in a shorter period of time, and the venous pump will complete its predetermined number of pump turns in a shorter period of time. The net result will be an increase in the number of milliliters of blood processed through the system each minute as the cycle time is shortened.

We claim:

1. An extracorporeal blood flow system for circulating blood of a patient comprising:
   a first, arterial blood pump having an input adapted to receive blood of a patient and an output;
   blood processing apparatus having an input coupled to the output of said arterial blood pump and an output;
   a second, venous blood pump having an input coupled to the output of said blood processing apparatus and an output adapted to provide processed blood;
   means, coupled to said first and second blood pumps, for producing information indicative of the speeds of said blood pumps;
   means, coupled to said speed information producing means, for converting said speed information to flowrate information of said pumps;
   means, responsive to said flowrate information produced by said converting means, for determining mean blood flowrate;
   a pump speed ratio control which produces an output signal indicative of a desired pump speed ratio; and
   pump speed control means, coupled to said blood pumps and responsive to said mean blood flowrate determination and said desired pump speed ratio, for controlling said pump speeds in accordance with said desired pump speed ratio so as to maintain a desired mean blood flowrate.

2. The arrangement of claim 1, wherein said speed information converting means converts the speed of said arterial blood pump to a flowrate value $Q_A$, and converts the speed of said venous blood pump to a flowrate value $Q_V$; and wherein said means responsive to said flowrate information determines mean blood flowrate in accordance with the expression $$Q_M = \frac{R}{R+1} Q_A,$$

where R is equal to $Q_V/Q_A$, and $Q_M$ is mean blood flowrate.

3. The arrangement of claim 1, wherein said speed information converting means converts the speed of said arterial blood pump to a flowrate value $Q_A$, and converts the speed of said venous blood pump to a flowrate value $Q_V$; and wherein said means responsive to said flowrate information determines means blood flowrate in accordance with the expression $$Q_M = \frac{1}{R+1} Q_V$$

where R is equal to $Q_V/Q_A$, and $Q_M$ is mean blood flowrate.

4. The arrangement of claim 1, further comprising:
   a pump speed control, coupled to said pump speed control means, for providing a signal representing a desired pump speed,
   whereby said pump speed control may be adjusted to alter said desired means blood flowrate.

5. An extracorporeal blood flow system for circulating blood of a patient comprising:
   a first, arterial blood pump having an input adapted to receive blood of a patient and an output;
   blood processing apparatus having an input coupled to the output of said arterial blood pump and an output;
   a second, venous blood pump having an input coupled to the output of said blood processing apparatus and an output adapted to provide processed blood;
   means, coupled to said first and second blood pumps, for producing information indicative of the speeds of said blood pumps;
   means, coupled to said speed information producing means, for converting said speed information to flowrate information of said pumps;
   a mode selection switch which provides a signal indicative of the selection of a single pump mode or a double pump mode; and
   means, responsive to said flowrate information produced by said converting means, and to said mode selection signal, for providing an indication of means blood flowrate when said double pump mode is selected, and for providing an indication of the flowrate of said arterial blood pump when said single pump mode is selected;
   a pump speed control for producing a signal representing a desired pump speed;
   a pump speed ratio control which produces an output signal indicative of a desired pump speed ratio when said system is operating in said double pump mode;
   pump speed control means, responsive to said desired pump speed signal and said pump speed ratio signal, and coupled to said blood pumps for controlling the speeds of said blood pumps; and
   whereby said mean blood flowrate and said arterial blood pump flowrate may be altered by adjusting said pump speed control when said system is operating in said respective modes.

6. A method for setting the blood flowrate of a hemodialysis system which includes an arterial blood pump adapted to periodically withdraw blood from a patient, a venous blood pump adapted to periodically return blood to said patient, and a dialyzer coupled between said blood pumps, comprising the steps of:
- (a) measuring the speeds of said arterial and venous blood pumps;
- (b) converting said measured speeds to blood flowrate values $Q_A$ and $Q_V$ of the respective pumps;
- (c) determining mean blood flowrate in accordance with the expression $$Q_M = \frac{R}{R+1} Q_A$$

where R is equal to $Q_V/Q_A$ and $Q_M$ is mean blood flowrate; and
- (d) adjusting the speeds and ratio of speeds of said blood pumps to produce a desired mean blood flowrate.

7. A method for setting the blood flowrate of a hemodialysis system which includes an arterial blood pump adapted to periodically withdraw blood from a patient, a venous blood pump adapted to periodically return blood to said patient, and a dialyzer coupled between said blood pumps, comprising the steps of:
- (a) measuring the speeds of said arterial and venous blood pumps;
- (b) converting said measured speeds to blood flowrate values $Q_A$ and $Q_V$ of the respective pumps;
- (c) determining mean blood flowrate in accordance with the expression $$Q_M = \frac{1}{R+1} Q_V$$

where R is equal to $Q_V/Q_A$ and $Q_M$ is mean blood flowrate; and
- (d) adjusting the speeds and ratio of speeds of said blood pumps to produce a desired mean blood flowrate.

* * * * *